United States Patent [19]

Dürsch

[11] 4,086,359

[45] Apr. 25, 1978

[54] DERIVATIVES OF PLEUROMUTILIN AND COMPOSITIONS

[75] Inventor: Friedrich Dürsch, Hopewell, N.J.

[73] Assignee: E. R. Squibb & Sons, Inc., Princeton, N.J.

[21] Appl. No.: 709,983

[22] Filed: Jul. 30, 1976

Related U.S. Application Data

[63] Continuation-in-part of Ser. No. 618,087, Sep. 30, 1975, abandoned.

[51] Int. Cl.$^2$ .................. A01N 9/24; C07C 143/12
[52] U.S. Cl. .................................... 424/299; 560/153
[58] Field of Search ............... 424/299; 260/481 R; 560/153

[56] References Cited

U.S. PATENT DOCUMENTS

3,919,290  11/1975  Egger ........................... 260/481 R

FOREIGN PATENT DOCUMENTS

2,248,237  4/1973  Germany.

OTHER PUBLICATIONS

Antimicrobial Agents & Chemotheraphy, May 1975, pp. 507–516, 517–521.

Primary Examiner—Allen J. Robinson
Attorney, Agent, or Firm—Lawrence S. Levinson; Merle J. Smith

[57] ABSTRACT

A new neutral fumarate salt of a derivative of the antibiotic pleuromutilin has been found whose physical properties made bulk manufacture more reproducible, simplify formulation and provide advantages in the administration of the substance.

9 Claims, No Drawings

DERIVATIVES OF PLEUROMUTILIN AND COMPOSITIONS

This application is a continuation-in-part of application Ser. No. 618,087, filed Sept. 30, 1975, now abandoned.

BACKGROUND OF THE INVENTION

Pleuromutilin (also now known as pleuromulin) is an antibiotic produced by cultures of the basidiomycete *Pleurotus mutilis*. The antibiotic has antibacterial activity. A group of new derivatives of pleuromutilin having antibacterial activity is described in German Offenlegungschrift No. 2,248,237 (Apr. 12, 1973). One of these derivatives in particular, 14-dioxy-14-[(2-diethylaminoethyl)mercaptoacetoxy]mutilin (known generically as tiamutilin or tiamulin), as the hydrogen fumarate salt, has been found to be very active against microorganisms such as Streptococci, Staphylococci and Mycoplasmas and particularly useful in veterinary medicine. See Antimicrobial Agents and Chemotherapy, May 1975, pages 507–516, 517–521. This substance, however, causes difficulties in manufacture, formulation and administration. Research on the substance has now demonstrated that the formation of the neutral fumarate salt provides a material at least equally active on a weight basis but which has markedly different physical properties which overcome the more serious disadvantages of the hydrogen fumarate.

DETAILED DESCRIPTION OF THE INVENTION

This invention relates to the new compound 14-dioxy-14-[(2-diethylaminoethyl)mercaptoacetoxy]mutilin neutral fumarate and to compositions containing it. [See Hodgin et al., Eur. J. Biochem. 47, 527–533 (1974) for the structure and this system of nomenclature.]This compound can also be named as the 14-(2-diethylaminoethyl)thioacetate ester of mutilin, neutral fumarate salt. By neutral fumarate salt is meant the salt containing one mole of fumaric acid and two moles of 14-deoxy-14-[(2-diethylaminoethyl)mercaptoacetoxy]mutilin, i.e., both acid groups of the fumaric acid are neutralized. [For convenience, 14-deoxy-14-[(2-diethylaminoethyl)mercaptoacetoxy]mutilin is referred to hereinafter for brevity as mutilin derivative.] This is distinguished from the hydrogen fumarate discussed in the two articles in Antimicrobial Agents and Chemotherapy, supra, which contains one mole of fumaric acid and one mole of mutilin derivative.

The mutilin derivative is difficult to isolate from the impurities and by-products found in the reaction mixture in which it is produced. Tiamutilin forms few readily isolatable salts. One of these is the salt with fumaric acid. It has been found, however, that even the previously used hydrogen fumarate requires numerous steps for isolation and purification involving formation of a non-aqueous solvent adduct and employment of several solvents in large amounts which must then be disposed of.

By forming the neutral fumarate under conditions as described below, a reproducible, readily crystallizable salt is formed in one step.

The new neutral fumarate is produced from the mutilin derivative (produced as described in German Offenlegungschrift No. 2,248,237) by adding one mole of fumaric acid to two moles of mutilin derivative. The mutilin derivative is preferably dissolved in a solvent in which the final product is insoluble, e.g., isobutyl acetate (which is preferred), butanol, ethyl acetate, methyl isobutyl ketone, xylene or the like. The fumaric acid can be added as a solid but it is preferably added as a concentrated solution in dimethylformamide.

By adding the fumaric acid to the solution of mutilin derivative the neutral fumarate is formed in high yield in the form of well developed prisms. When the order of addition is reversed, i.e., the mutilin derivative is added to the fumaric acid, then the tendency is to form the hydrogen fumarate salt. The crystalline neutral fumarate product is isolated by filtration or centrifugation, washing with the same solent and drying.

According to the preferred method, the crude mutilin derivative, as the free base, in the reaction mixture is extracted into isobutyl acetate, a solution containing fumaric acid in dimethylformamide is added to the isobutyl acetate solution in a proportion of one mole of fumaric acid to two moles of mutilin derivative at room temperature. The precipitated crystalline product is then isolated by filtering or centrifuging.

The neutral fumarate is obtained in crystalline form which has properties distinct from the hydrogen fumarate. A comparison of properties of the neutral fumarate and hydrogen fumarate is as follows:

| Property | Neutral fumarate | Hydrogen fumarate |
|---|---|---|
| Molecular weight | 1103.5 | 609.8 |
| Melting point, ° C | 137–138 | 147–149 |
| Solubility in Water at 25° C, g/ltr | 380 | 70 |
| pH of Saturated Solution | 4.9 | 3.3 |
| Bulk Density gm/cc | 0.5 | 0.27 |
| Hygroscopicity at 70% r.h. and 25° C | none | none |
| Residual Solvents | traces | traces |
| Volatiles in Wet Cake, % w/w | <10 | >30 |
| Active Base in Salt, % w/w | 89.5 | 81.0 |
| Crystal Form | Stout Prisms | Thin Plates and needles |

The new neutral fumarate of this invention overcomes various disadvantages encountered with the known hydrogen fumarate in various areas. In manufacturing, the hydrogen fumarate has a tendency to form polymorphs and solvates which make it difficult to reliably reproduce acceptable crystals on a bulk manufacturing scale. No solvates of the neutral fumarate have been encountered in manufacturing so reproducible results are consistently obtained.

The hydrogen fumarate which is obtained in the form of fine crystals shows a tendency to disperse into the atmosphere and cause the handlers to sneeze, thus providing a hazard to the manufacturing workers. The neutral fumarate is characterized by large crystal size and high bulk density and does not display this tendency. The large prisms in which the neutral fumarate forms are easily obtained in pure form during manufacture and are easy to handle.

The amount of volatiles retained in the wet cake after production of the salt, as seen from the table, is greater than 30% in the case of the hydrogen fumarate compared with less than 10% (usually about 8%) for the neutral fumarate. This makes it easier to work up the neutral fumarate, requiring less washing of the cake to remove impurities.

From the point of view of formulation, the high bulk density of the neutral fumarate simplifies formulation work, especially in tablets and capsules. The product is useful in preparing injectable compositions, particularly for larger animals like pigs and cattle, and also to produce concentrates for dilution with drinking water in automatic proportioning devices like "Auto-medic' used in administering medicaments to poultry.

The higher pH of the neutral fumarate in solution is an advantage from the point of view of irritation at the site of injection since it is known that such irritation occurs more frequently as the pH decreases. In addition, the local tolerance on injection is improved when the neutral fumarate is used.

The neutral fumarate is at least as active as the hydrogen fumarate in vitro and in vivo on a weight basis. The product is thus useful as an antibacterial agent, particularly in veterinary medicine, for the treatment of a variety of infections particularly against pathogenic gram positive bacteria such as Streptococci and Staphylococci as well as Mycoplasma and Treponema. Some gram positive organisms such as Shigella, Klebsiella and Escherichia coli are also responsive to this substance.

The neutral fumarate of 14-deoxy-14-[(2-diethylaminoethyl)mercaptoacetoxy]mutilin is useful for the treatment of swine dysentery (due to *Treponema hyodysenteriae*), enzootic pneumonia of pigs, atrophic rhinitis in pigs, mycoplasmosis, chronic respiratory disease in poultry (CRD), air sac disease, infectious synovitis, fowl cholera, bovine pneumonia, respiratory infections of horses, sheep, dogs, cats, etc.

The substance can be administered orally in drinking water or in feed compositions or parenterally in a physiologically acceptable vehicle or carrier such as water, which is the preferred carrier, aqueous ethanol solutions, naturally occurring vegetable oil or physiologically acceptable modified naturally occurring oils or synthetic oils. Effective doses lie in the range of 1 to 50 mg/kg, preferably about 5 to 20 mg/kg. Compositions containing the 14-deoxy-14-[(2-diethylaminoethyl)mercaptoacetoxy]mutilin neutral fumarate, depending on the intended use and mode of administration as discussed below, can contain about 0.002 to 20% by weight of active substance. The preferred mode of administration is by intramuscular injection. The vehicle can be sterile water for injection, aqueous ethanol solutions, naturally occurring vegetable oil solutions, e.g., corn oil, sesame oil, coconut oil, cottonseed oil and the like, or synthetic oil solutions, e.g., ethyl oleate, fractionated coconut oil, etc. The drug is administered utilizing sufficient material in about 5 to 10 ml. of vehicle, providing concentrations of about 5 to 20% (weight-/vol.). The dosage is in general administered 1 to 2 times daily for 5 to 10 days.

Other substances can be included in the formulations as required to produce a stable composition of pharmaceutical elegance. For example, the composition can include preservatives like phenol, chlorobutanol, methyl paraben, propyl paraben or benzyl alcohol, antioxidants like BHT (butylated hydroxytoluene), BHA (butylated hydroxyanisole), buffering agents, etc. as required by conventional pharmaceutical practice in formulating drug compositions, especially for veterinary use.

The neutral fumarate of this invention can also be administered by other methods. For example, it can be administered to poultry for the treatment of Mycoplasma infections in the drinking water. The active material is dissolved in the water for the poultry at a concentration of about 0.002 to 2%, preferably about 0.005 to 0.05% (wt/vol). Treatment is usually continued for about 7 to 10 days. Concentrates for liquid proportioning devices containing 2 ounces per gallon for mixing with 128 gallons water provide a 0.016% solution.

The medicament can also be administered by incorporating the substances in animal feed compositions, e.g., swine starter rations, grower and finisher rations, starter and finisher rations for broiler chickens and turkeys, layer rations, etc. Such compositions are generally prepared as concentrated feed premixes (containing about 50 to 500 gm., preferably 50 to 250 gm. of medicament per pound of premix material) which are then incorporated in the bulk animal feed material resulting in a concentration of about 50 to 500 gm. of neutral fumarate per ton of feed composition.

The following examples are illustrative of the invention.

EXAMPLE 1

Preparation of 14-Deoxy-14-[(2-diethylaminoethyl)mercaptoacetoxy]mutilin Neutral Fumarate From Pleuromutilin Tosylate Pleuromutilin tosylate (53.3 grams) and β-diethylaminoethanethiol hydrochloride (18.7 grams) are stirred with acetone (160 ml.) in an ice bath. After cooling to +5° C, a methanolic solution of sodium methylate (50 ml. of a 25% solution) is added in one portion. The temperature rises rapidly to about 30° C. The mixture is again cooled to 20° C. and isobutyl acetate (250 ml.) and water (250 ml.) are added. The batch is equilibrated and the layers are allowed to separate. The aqueous layer is discarded. The organic layer is stirred with water (100 ml.) and sufficient dilute HCl to lower the pH to 6.5. The aqueous phase, containing disulfide impurities, is again discarded. The organic phase is then extracted with 1 N HCl (100 ml.), followed by water (25 ml.). The combined aqueous layers are made basic with 1N NaOH (105 ml.) to a pH above 8 in the presence of fresh isobutyl acetate (150 ml.). The mixture is equilibrated, the phases are allowed to separate and the aqueous layer is discarded. The organic layer is dried over MgSO$_4$ and is polish filtered. The filtrate contains the desired mutilin derivative as the free base. Titration indicates a yield of about 92–94 mole%, based upon pleuromutilin tosylate pleuromutilintosylate input.

The equivalent amount of fumaric acid (5.3 grams) is dissolved in dimethylformamide (17.5 ml.). About 10% of this solution is added with stirring to the solution of the free base from above. Crystallization is allowed to proceed for about 10 minutes, in the presence of some seeds of the desired product. Subsequently, the remainder of the fumaric acid solution is added and the crystallization is completed by stirring for two hours at room temperature.

The crystals are collected on a filter and are washed with fresh isobutyl acetate (about 50 ml.). Drying furnishes pure 14-deoxy-14[(2-diethylaminoethyl)mercaptoacetoxy]mutilin neutral fumarate (37 grams, corresponding to 67 mole %, based upon the pleuromutilin tosylate input).

Most of the mutilin derivative remaining in the mother liquors (about 22 mole %, based upon the pleuromutilin tosylate input) is recovered by washing the liquid with aqueous sodium hydroxide to remove fumaric acid, followed by extraction into aqueous hydrochloric acid at a pH below 2. This acidic extract is then returned into a subsequent batch for a substantial overall yield increase.

EXAMPLE 2

A solution of the free base of the mutilin derivative in isobutyl acetate is prepared as described in Example 1. The solution is heated to about 60°–70° C. and the equivalent amount of solid fumaric acid (5.3 grams) is added in one portion with efficient agitation. The fumaric acid dissolves gradually and the characteristic prismatic crystals of the desired product separate. The mixture is allowed to cool to room temperature and the crystallization is completed by stirring for two more hours. The crystals are collected on a filter and are washed with fresh isobutyl acetate (75 ml.). Drying furnishes pure 14-deoxy-14-[(2-diethylaminoethyl)mercaptoacetoxy]-mutilin neutral fumarate (46.3 grams of 84 mole %, based upon the pleuromutilin tosylate charged).

EXAMPLE 3

14-Deoxy-14-[(2-diethylaminoethyl)mercaptoacetoxy]mutilin is produced as described in Example 1 and the mixture is worked up to the aqueous acidic extract. For the subsequent back-extraction, ethyl acetate (200 ml.) is substituted for the isobutyl acetate. The extract is dried and filtered as described in Example 1. Titration indicates the presence of about 92 mole % of the free base of the mutilin derivative in the filtrate.

The equivalent amount of fumaric acid is added as a solid to the stirred filtrate as reflux temperature. The fumaric acid dissolves quickly and the neutral fumarate salt separates in the form of prismatic crystals. The mixture is cooled to room temperature and crystallization is completed by stirring for two additional hours. Filtration, washing with fresh ethyl acetate (50 ml.) and drying furnishes pure 14-deoxy-14-[(2-diethylaminoethyl)mercaptoacetoxy]mutilin neutral fumarate (42.4 grams or 77 mole %, based upon the pleuromutilin tosylate input).

EXAMPLE 4

A 10% multiple dose solution is prepared by dissolving 1 kg. of 14-deoxy-14-[(2-diethylaminoethyl)-mercaptoacetoxy]mutilin neutral fumarate in 10 liters of a 50% solution of aqueous ethanol at room temperature. The solution is bottled in 100 ml. multi-dose bottles. This solution is administered intramuscularly to pigs infected with swine dysentery in 1 to 10 ml. dosages (10 mg/kg) once daily for five days.

EXAMPLE 5

1 kg. of 14-deoxy-14[(2-diethylaminoethyl)mercaptoacetoxy]mutilin neutral fumarate is mixed with 5 liters of ethyl oleate under sterile conditions until thoroughly suspended. 5 mg. of a mixture of methyl paraben and propyl paraben (10:1) are added. The 20% oil suspension is bottled in 100 ml. multiple dose bottles for intramuscular injection.

EXAMPLE 6

500 gm. of 14-deoxy-14-[(2-diethylaminoethyl)mercaptoacetoxy]mutilin neutral fumarate are suspended in 10 liters of fractionated coconut oil (Neobee 20) and 100 mg. of benzyl alcohol are added under sterile conditions. The 5% suspension is subdivided into sterile vials each containing 5 ml. for intramuscular injection.

EXAMPLE 7

An aqueous concentrate for use in a liquid proportioning device like "Auto-Medic" is prepared by dissolving 6 kg. of 14-deoxy-14-[(2-diethylaminoethyl)-mercaptoacetoxy]mutilin neutral fumarate in 100 gal. of water. 3.78 kg. of benzyl alcohol are added. The solution is bottled in 1 gal. bottles. The contents of one bottle are placed in a liquid proportioning device adjusted to mix with 128 gal. of water to provide a 0.0125% concentration drinking water solution for administration to broiler chickens infected with CRD.

EXAMPLE 8

A feed premix is prepared by thoroughly admixing 10 kg. of 14-deoxy-14-[(2-diethylaminoethyl)mercaptoacetoxy]mutilin neutral fumarate with 100 lb. of soybean meal. The mixture is subdivided into packages each containing 100 gm. of active ingredient per lb. of premix. Two lbs. of premix is added to one ton of feed to provide a medicated feed containing 200 gm. per ton.

EXAMPLE 9

A swine starter ration is admixed consisting of the following ingredients

|  | Lbs |
|---|---|
| Corn meal | 1315 |
| Wheat midds | 100 |
| Soybean | 405 |
| Menhaden meal | 40 |
| Dried Whey | 50 |
| Calcium phosphate | 30 |
| Salt | 10 |
| Molasses | 50 |
|  | 2000 |

To the swine starter ration is added 100 gm of 14-deoxy-14-[(2-diethylaminoethyl)mercaptoacetoxy]-mutilin neutral fumarate and the mixture is thoroughly blended. The feed composition contains 100 gm. of active medicament per ton of feed. The medicated feed composition is fed to 5 to 8 week old pigs infected with *Treponema hyodysenteriae* for 14 days.

EXAMPLE 10

A swine starter ration is prepared containing the following ingredients:

|  | Lbs |
|---|---|
| Corn meal | 1311 |
| Wheat midds | 100 |
| Soybean | 405 |
| Menhaden meal | 40 |
| Dried Whey | 50 |
| Calcium phosphate | 30 |
| Salt | 10 |
| Molasses | 50 |
| Mineral Mix | 2 |
| Vitamin Mix | 2 |
|  | 2000 |

The mineral mix is made up in the following proportions:

|  | Gm |
|---|---|
| Copper | 5.4 |
| Iron | 68.0 |
| Manganese | 18.2 |
| Zinc | 45.4 |

-continued

|  | Gm |
|---|---|
| Iodine | 0.2 |

The vitamin mix is made up in the following proportions:

| Vitamin A | 3000 IU |
|---|---|
| Vitamin D | 1000 IU |
| Vitamin E | 20 IU |
| Vitamin $B_{12}$ | 20 μg |
| Riboflavin | 3 mg |
| Pantothenic acid | 10 mg |
| Niacin | 20 mg |
| Choline | 200 mg |

The feed composition including vitamin and mineral mixes is thoroughly admixed with 200 gms. of 14-deoxy-14-[(2-diethylaminoethyl)mercaptoacetoxy]-mutilin neutral fumarate providing a medicated feed composition containing 200 gm. of active ingredient per ton of feed. Pigs infected with *Treponema hyodysenteriae* are permitted to feed ad libitum on this feed composition for 14 days.

What is claimed is:

1. 14-Deoxy-14-[(2-diethylaminoethyl)mercaptoacetoxy]mutilin neutral fumarate.

2. A veterinary composition comprising about 0.002 to 20 % by weight of 14-deoxy-14-[(2-diethylaminoethyl)mercaptoacetoxy]mutilin neutral fumarate and a physiologically acceptable vehicle therefor.

3. A veterinary composition for intramuscular injection comprising about 5 to 20% by weight of 14-deoxy-14-[(2-diethylaminoethyl)mercaptoacetoxy]mutilin neutral fumarate and a physiologically acceptable vehicle therefor.

4. A medicated animal feed composition comprising about 50 to 500 gm. per ton of 14-deoxy-14-[(2-diethylaminoethyl)mercaptoacetoxy]mutilin neutral fumarate in an animal feed composition.

5. A concentrated premix for animal feed compositions comprising about 50 gm. to 500 gm. per pound of 14-deoxy-14-[(2-diethylaminoethyl)mercaptoacetoxy]-mutilin neutral fumarate and a physiologically acceptable vehicle therefor.

6. An aqueous medicated concentrate for oral administration to poultry comprising about 2 ounces of 14-deoxy-14[(2-diethylaminoethyl)mercaptoacetoxy]mutilin neutral fumarate per gallon of water.

7. A method for treating bacterial infections in animals which comprises administering orally or parenterally to an animal with a bacterial infection about 1 to 50 mg./kg. of 14-deoxy-14-[(2-diethylaminoethyl)mercaptoacetoxy]mutilin neutral fumarate in a physiologically acceptable vehicle therefor.

8. A method as in claim 7 wherein the dosage is about 5 to 20 mg/kg.

9. A method for treating swine dysentery which comprises administering to an infected pig about 5 to 20 mg./kg. of 14-deoxy-14-[(2-diethylaminoethyl)mercaptoacetoxy]mutilin neutral fumarate in a physiologically acceptable vehicle therefor.

* * * * *

UNITED STATES PATENT AND TRADEMARK OFFICE
CERTIFICATE OF CORRECTION

PATENT NO. : 4,086,359
DATED : April 25, 1978
INVENTOR(S) : Friedrich Dursch

It is certified that error appears in the above–identified patent and that said Letters Patent are hereby corrected as shown below:

Column 1, line 16 "dioxy" should read -- deoxy --
Column 1, line 35 "dioxy" should read -- deoxy --
Column 2, line 14 "solent" should read -- solvent --
Column 3, line 5 "Auto-medic' should be in full quotes
Column 4, line 47 "pleuromutilintosylate" should be deleted
Claim 6, Column 8, line 17 insert a hyphen after "14"

Signed and Sealed this

*Fifteenth* Day of *May 1979*

[SEAL]

*Attest:*

RUTH C. MASON
*Attesting Officer*

DONALD W. BANNER
*Commissioner of Patents and Trademarks*